(12) United States Patent
Munro et al.

(10) Patent No.: US 8,871,992 B2
(45) Date of Patent: Oct. 28, 2014

(54) MULTILAYER COMPOSITIONS AND DRESSINGS

(75) Inventors: Hugh Semple Munro, Chipping Campden (GB); Philip Andrews, Wiltshire (GB)

(73) Assignee: First Water Limited, Wiltshire (GB)

( * ) Notice: Subject to any disclaimer, the term of this patent is extended or adjusted under 35 U.S.C. 154(b) by 87 days.

(21) Appl. No.: 13/260,669

(22) PCT Filed: Mar. 24, 2010

(86) PCT No.: PCT/GB2010/050501
§ 371 (c)(1),
(2), (4) Date: Dec. 19, 2011

(87) PCT Pub. No.: WO2010/109239
PCT Pub. Date: Sep. 30, 2010

(65) Prior Publication Data
US 2012/0116279 A1    May 10, 2012

(30) Foreign Application Priority Data
Mar. 27, 2009 (GB) .................................... 0905290

(51) Int. Cl.
*A61F 13/00* (2006.01)
(52) U.S. Cl.
USPC .............................................. 602/43; 602/46
(58) Field of Classification Search
USPC ..................................................... 602/41–54
See application file for complete search history.

(56) References Cited

U.S. PATENT DOCUMENTS

| 5,330,452 A | 7/1994 | Zook |
| 5,643,187 A | 7/1997 | Naestoft et al. |
| 5,891,076 A | 4/1999 | Fabo |
| 6,384,294 B1 * | 5/2002 | Levin .............................. 602/41 |
| 6,727,402 B1 | 4/2004 | Bruss et al. |
| 2003/0114818 A1 * | 6/2003 | Benecke et al. .............. 604/378 |
| 2006/0148352 A1 | 7/2006 | Munro et al. |
| 2007/0282237 A1 | 12/2007 | Munro et al. |

FOREIGN PATENT DOCUMENTS

| EP | 0630629 A | 12/1994 |
| EP | 1649873 A2 | 4/2006 |
| WO | 9304691 A1 | 3/1993 |
| WO | 9310795 A1 | 6/1993 |

(Continued)

OTHER PUBLICATIONS

International Search Report dated Jun. 29, 2010 from PCT/GB2010/050501.

(Continued)

*Primary Examiner* — Michael A. Brown
(74) *Attorney, Agent, or Firm* — Nixon Peabody LLP; Ronald I. Eisenstein; Susanna C. Benn (57) ABSTRACT

The invention provides a layered composition comprising: a first layer comprising a first material, wherein the first material comprises a gel material; a second layer comprising a second material, wherein the second material is harder is than the first material; and a third layer comprising a third material, wherein the third material has a lower tensile modulus than the second material, wherein the second layer is disposed between the first and third layers. The composition may be used in a wound dressing, in which preferably the first layer is in fluid flow communication with the wound.

14 Claims, 1 Drawing Sheet

(56) References Cited

FOREIGN PATENT DOCUMENTS

| WO | 93/19710 | A1 | 10/1993 |
|---|---|---|---|
| WO | 9602270 | A1 | 2/1996 |
| WO | 9724149 | A1 | 7/1997 |
| WO | 9734947 | A1 | 9/1997 |
| WO | 0006214 | A1 | 2/2000 |
| WO | 0006215 | A1 | 2/2000 |
| WO | 0007638 | A1 | 2/2000 |
| WO | 0046319 | A1 | 8/2000 |
| WO | 0065143 | A1 | 11/2000 |
| WO | 0196422 | A1 | 12/2001 |
| WO | 2005/016179 | A2 | 2/2005 |
| WO | 2007007115 | A2 | 1/2007 |
| WO | 2007007155 | A1 | 1/2007 |

OTHER PUBLICATIONS

Hydrogels, Kirk-Othmer Encyclopedia of Chemical Technology. John Wiley and Sons, New York. 4th ed., vol. 7. 783-807. Print.
Oxyzyme System, www.wounds-uk.com/posterabstracts2003.pdf.

* cited by examiner

MULTILAYER COMPOSITIONS AND DRESSINGS

CROSS REFERENCE TO RELATED APPLICATIONS

The present application is a 35 U.S.C. §371 National Phase Entry Application of International Application No. PCT/GB2010/050501 filed Mar. 24, 2010, which designates the U.S., and which claims the benefit under 35 U.S.C. §119(b) to GB application No. 0905290.3 filed Mar. 27, 2009 the contents of which are incorporated herein by reference in their entirety.

FIELD OF INVENTION

The present invention relates to multilayer compositions and their use as wound dressings. They may be for use in or as wound dressings, particularly when absorption of fluid may be required. Such dressings may also be used for the treatment of blisters, minor wounds and chafe wounds, as well as prophylactically to avoid the same, for example in connection with the practice of sports or manual labor and the like, where the skin areas, such as heels, elbows, knees and palms of the hand are subject to particularly severe stresses which easily give rise to the above-mentioned minor injuries. The invention also relates to processes for the manufacture of the compositions, and to uses of these dressings.

The expressions "hydrogel" and "hydrogel composites" used herein are not to be considered as limited to gels which contain water, but extend generally to all hydrophilic gels and gel composites, including those containing organic non-polymeric components in the absence of water.

BACKGROUND OF THE INVENTION

The complex interaction of the factors associated with foot blisters, minor wounds, chafe wounds and skin breakdown in general, creates a technological challenge: how to design dressings that provide adequate mechanical stability while protecting the soft tissues from trauma and where the skin has already undergone trauma, providing an appropriate therapeutic environment. It has been recognised that the construction of an appropriate dressing ideally will provide for an interface with the traumatised or non-traumatised skin which is soft and elastic and interface with the external environment, for examples clothes and shoes, which has good slip properties, i.e. a low coefficient of friction. Examples of dressings that address the interfacing problems can be found in U.S. Pat. No. 6,727,402 assigned to Beisdorf A G and U.S. Pat. No. 5,643,187 assigned to Coloplast A/S. Both of these documents describe that the external interfacing layer can be of a harder material than the skin-interfacing layer. The combination of the two layers with different hardness results in dressings with improved sliding properties. U.S. Pat. No. 5,643,187 teaches that the outer hard layer should be less than 10 microns (μm) and U.S. Pat. No. 6,727,402 teaches that the outer layer should be greater than 10 microns (μm). The hardness of a material may be determined by the Shore or Durometer scales according to, for example, the ASTM method D2240.

Whilst U.S. Pat. No. 5,643,187 and U.S. Pat. No. 6,727,402 represent improvements on the prior art, there is still a need for improved, economic, easy-to-manufacture dressings that address the technological design challenges presented by the different needs of the two interfaces.

The present invention as described below provides at least an alternative, optionally an improved, dressing over one or more of those disclosed in the prior art. The present invention may overcome or mitigate at least one or more problems associated with the dressings of the prior art.

BRIEF DESCRIPTION OF THE INVENTION

The present invention is based on our surprising discovery that a multilayer dressing comprising an intermediate layer comprising a hard material positioned between a skin interfacing layer comprising a gel, which may be viscoelastic, and external interfacing layer possessing a low coefficient of friction and/or greater extensibility than the intermediate layer, providing greater protection to the damaged and non damaged skin than previously known and also providing therapeutic value can be easily and economically made.

In a first aspect, the present invention provides a layered composition comprising:
a first layer comprising a first material, wherein the first material comprises a gel material;
a second layer comprising a second material, wherein the second material is harder is than the first material; and
a third layer comprising a third material, wherein the third material has a lower tensile modulus than the second material or wherein the third material is a low friction material, or both,
wherein the second layer is disposed between the first and third layers.

In an embodiment, the third material is a low friction material.

In a second aspect, the present invention provides a layered composition comprising:
a first layer comprising a first material, wherein the first material comprises a gel material;
a second layer comprising a sheet of a polymeric second material, for example a polyester; and
a third layer comprising a third material, which is a low friction material,
wherein the second layer is disposed between the first and third layers;
and wherein the layered composition has a microhardness according to BS ISO 48:2007 between about 30 International Rubber Hardness Degrees (IRHD) and about 90 IRHD, preferably between about 50 IRHD and about 90 IRHD, wherein the microhardness is measured according to a BS ISO 48 test standard.

The present inventors have found that when the composition of the first or second aspect is used as a wound dressing, particularly on wounds such as blisters, minor wounds and chafes, it provides a comfortable dressing that promotes wound healing and avoids or mitigates break-up of the softer gel material. Without being bound by theory, it is believed that the provision of a relatively hard intermediate (second) layer enhances the penetration resistance of the dressing and facilitates improved dispersion of forces applied to the dressing as may occur for example when the interfacing with the external environment of footwear and clothing. The harder intermediate layer also provides for an improved base for the third layer, which may be a low friction layer, resulting in the overall improved slip properties of the dressing. The harder intermediate layer also appears to impart improved mechanical stability to the gel material.

In a third aspect, the present invention provides a wound dressing comprising the layered composition of the first or second aspects.

In a fourth aspect, the present invention provides a composition of the first or second aspect for the prevention or treatment of a wound.

In a fifth aspect, the present invention provides a method of preventing or treating a wound comprising applying the composition of first or second aspect to a wound, if formed, and/or skin, wherein the first layer is disposed closer to the wound and/or skin than the third layer.

The first layer, in use, is preferably in fluid communication with the wound. At least part of one surface, optionally all of one surface, of the first layer and/or first material may be exposed for contacting a wound. Optionally, one or more further layers and/or materials may be disposed between the wound and the first layer. The one or more further layers may be porous. The one or more further layers may comprise a net member. The net member may be as described in EP-A-1649873, the disclosures in which are incorporated herein by reference.

In a sixth aspect, the present invention provides a method of manufacturing of a layered composition of the first or second aspect, the method comprising assembling the first, second and third layers to form the layered composition. The assembling may comprise adhering the first, second and third layers together, optionally with one or more further layers and/or materials disposed between the first and second layer and/or the second and third layer. The one or more further layers and/or materials may comprise one or more adhesive materials. The assembling may comprise forming one or more of the first, second and third layers, in situ, such that, once formed, the layer is adhered to one or more of the other layers in the composition.

The layered composition is preferably a flexible composition, preferably a skin conformable composition. The layered composition is preferably adapted to keeping a wound moist. The layered composition is preferably water-absorbent, preferably such that, when in place over a wound, the composition can absorb and optionally retain liquid wound exudate.

The first layer and/or first material is/are preferably compressible. The first material is preferably a self-supporting material. The first layer and/or first material, in use, preferably can removably adhere to skin and/or a wound. The first material preferably is such that it can maintain a moist wound environment when in place over a wound. The first material and/or gel material is preferably a viscoelastic material. Viscoelastic materials are known to the skilled person. A viscoelastic material typically has one or more of the following properties: (i) hysteresis in the material's stress-strain curve; (ii) stress relaxation occurs in the material: step constant strain causes decreasing stress; and (iii) creep occurs in the material: step constant stress causes increasing strain. A viscoelastic material typically loses energy when a load is applied and then removed. The first layer will typically comprise two opposing surfaces, which can be termed first and second surfaces, one of which may be exposed at least in part for contacting a wound.

The first material comprises a gel, preferably a hydrogel. A "gel" includes, but is not limited to, a self-supporting, flexible substance, optionally comprising one or more polymers. A gel may comprise water. The first material is preferably a viscoelastic hydrogel. The first layer may consist essentially of or consist of a gel, for example a hydrogel, and any water contained therein. "Consist essentially of" in this context includes, but is not limited to, the first layer comprising about 5 wt % or less, preferably about 2 wt % or less, of components other than the gel and any water it may contain.

The second layer may comprise two opposing surfaces, one or both of which may have a pressure sensitive adhesive thereon, for adhesion to one or more of the other layers in the composition, for example the first and/or third layers.

The third layer may extend beyond the margins of the first and/or second layer. The third layer will typically comprise two opposing surfaces, one of which, in use, will face the wound and the other of which will face away from the wound. One or both of the opposing surfaces of the third layer may have disposed thereon a pressure sensitive adhesive for adhesion to one or more other layers of the composite, for example the second layer. If the third layer extends beyond the margins of the first and/or second layers, at least part of the surface of the third layer which extends beyond the first and/or third layer may have a pressure sensitive adhesive, preferably a medical grade pressure sensitive adhesive, thereon for adhesion to the skin. The pressure sensitive adhesive may form a continuous or discontinuous coating on the skin-facing surface of the third layer. Preferably, the surface of the third layer facing away from the wound does not have an adhesive thereon. The surface of the third layer facing away from the wound may be the outermost surface of the layered composition. A surface of the third material may, in use, constitute at least part of, optionally all of, the outermost surface of the layered composition.

According to the invention, the second layer of the layered composition is disposed between the first and third layers. For avoidance of doubt, it is not essential that the second layer contacts either or both of the first and third layers, although it may contact one or both thereof. Interfacing layers, e.g. adhesive layers, scrim layers, net layers, etc may be present between the layers of the layered composition.

The relative hardness of the materials is preferably such that the first material has a lower hardness than the second material as measured on the Shore hardness scale.

Preferably, the relative hardness of the layers is such that the first layer has a lower hardness than the second layer as measured on the Shore hardness scale, preferably the Shore A hardness scale when measured in accordance with ASTM D2240.

The second layer and/or second material preferably comprises a film of material of Shore Hardness on the A scale greater than 40, preferably greater than 50 even more preferably greater than 60, as measured using ASTM method D2240.

The term "low friction material" used herein refers particularly to a material having a surface coefficient of friction which is low enough that clothing materials, such as cotton and/or polyester can slide (i.e. pass) easily over the surface of the material. The coefficient of friction may be a static or dynamic coefficient of friction. Measurement of static and dynamic coefficients of friction are known to those skilled in the art. The static and dynamic coefficients of friction may be measured using standard equipment, and may be carried out at standard temperature and pressure, for example 20° C. and 101.325 kPa. The static and dynamic coefficients of friction may be measured in accordance with ASTM D1894-08. Against a cotton material, the dynamic coefficient of friction of the third material may be about 1.5 or less, optionally about 1 or less, optionally about 0.9 or less. Against a Teflon® material, the dynamic coefficient of friction of the third material may be about 1 or less, optionally about 0.7 or less, optionally about 0.5 or less, optionally about 0.4 or less. The third material may have a low friction value as measured in accordance with ISO 8295, 1986, in the test described in U.S. Pat. No. 5,643,187 in column 11, lines 18 to 21. The friction may be measured as the dynamic friction according to ISO 8295, 1986, the base used being a Teflon® coated glass tissue of the type: Acoflon G 13 A from Aco-plast A/S, Helsingor, DK, the weight of the carriage being 500 g. This test may be carried out at standard temperature and pressure, for example 20° C. and 101.325 kPa. The frictional value of the third material, for example when in the form of a sheet, in N, when measured in accordance with this test may be about 5 or less, preferably about 3 or less, more preferably about 2 or less.

Release liner layers may be applied to the exposed upper and lower surface of the multilayer dressing to facilitate ease of handling and packaging.

The expression "wound" and like expressions, used herein, include, but are not limited to, skin lesions in human and other mammalian skin, for example cuts, grazes, abrasions, tears, bums, scalds, ulcers, spots, blisters, and chafe wounds. The wound can, for example, be dermal, epidermal, or a combination of both. The wound may be an acute or chronic wounds. Chronic wounds are described in more detail in WO 2007/007115, the disclosures in which are incorporated herein by reference.

The composition and/or dressing may be used to prevent or treat a wound in a human or animal subject.

BRIEF DESCRIPTION OF THE DRAWINGS

An embodiment of the present invention will now be described further, without limitation and purely by way of example, with reference to the accompanying drawing, in which.

A non-limiting embodiment of the present invention is now further described with reference to FIG. 1.

Figure 1:
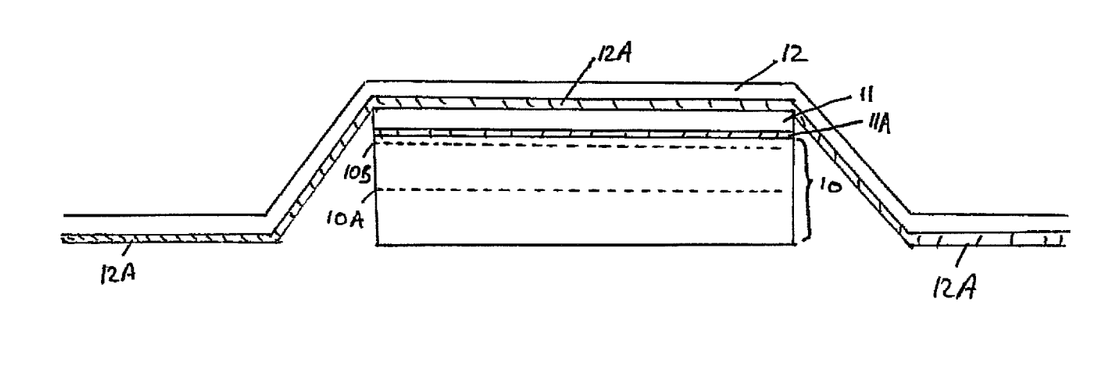
FIG. 1 illustrates in transverse cross-section the structure of an embodiment of the composition and dressing according to the present invention.

FIG. 1 shows the multilayered structure comprising three main layers 10, 11 and 12.

Layer 10 comprises a water absorbent gel, preferably a hydrogel, that contacts the damaged skin and or skin to be protected. It optionally comprises one or more porous scrims as shown by 10A and 10B.

Layer 11 comprises a preferably continuous structure comprising a material harder than layer 12 and layer 10. There is an optional layer 11A comprising a pressure sensitive adhesive.

Layer 12 is the external interfacing layer and comprises a low friction film with an optional layer 12A, comprising a pressure sensitive adhesive.

DETAILED DESCRIPTION OF THE INVENTION

In an embodiment, the first layer may be thicker than the second layer. In an embodiment, the second layer may be thicker than the third layer.

The first layer may have a thickness of about 0.1 mm or more, more preferably about 0.3 mm or more, and even more preferably about 0.5 mm or more.

The second layer may have a thickness of about 0.02 mm or more, more preferably about 0.05 mm or more, and even more preferably about 0.09 mm or more. The second layer preferably has a thickness of about 0.2 mm or less, more preferably about 0.17 mm or less.

The third layer, inclusive of an optional adhesive layer which may be disposed on a surface of the third layer, may have a thickness of about 0.01 mm or more, more preferably about 0.02 mm or more and even more preferably about 0.025 mm or more.

The gel in first layer preferably comprises a hydrocolloid, a hydrogel or other viscoelastic gel.

The gel in the first layer preferably has a hardness (as measured in accordance with ASTM2240) of about 40 or less on the Shore A scale, even more preferably about 20 or less on the Shore A scale. The hardness measurement of the gel material and all other layers and materials as described herein may be carried out using standard equipment, and may be carried out at standard temperature and pressure, for example 20° C. and 101.325 kPa. The gel may comprise, consist essentially of or consist of a cross-linked hydrophilic polymer of a hydrophilic monomer and optionally one or more comonomers, together with water and/or one or more organic plasticiser, and optionally together with one or more additives selected from surfactants, polymers, pH regulators, electrolytes, chloride sources, bioactive compounds (including antimicrobial agents) and mixtures thereof, with less than about 30% by weight of other additives.

The first layer may comprise a hydrocolloid. The hydrocolloid may be selected from sodium carboxymethylcellulose, pectin, gelatine, guar gum, locust bean gum, karaya gum, and mixtures thereof.

Preferably, the first layer comprises a hydrogel. The expression "hydrogel" and like expressions, used herein, are not to be considered as limited to gels which contain water, but extend generally to all hydrophilic gels, including those containing organic non-polymeric components in the absence of water. The gel forming agent may, for example, be selected from natural hydrophilic polymers, synthetic hydrophilic polymers, hydrocolloids, gelling hydrophilic biopolymers and all combinations thereof.

Hydrogels are, generally speaking, hydrophilic polymers characterized by their hydrophilicity (i.e capacity to absorb large amounts of fluid such as wound exudate) and insolubility in water: i.e. they are capable of swelling in water while generally preserving their shape.

The hydrophilicity is generally due to groups such as hydroxyl, carboxy, carboxamido, and esters, among others. On contact with water, the hydrogel assumes a swollen hydrated state that results from a balance between the dispersing forces acting on hydrated chains and cohesive forces that do not prevent the penetration of water into the polymer network. The cohesive forces are most often the result of crosslinking, but may result from electrostatic, hydrophobic or dipole-dipole interactions.

Useful classes of hydrogels in the present invention include those polymers and copolymers derived from acrylic and methacrylic acid ester, including hydroxyalkyl(meth)acrylates, 2-(N,N-dimethylamino)ethyl methacylate, methacryloyloxyalkyl sulfonates (generally crosslinked with diacrylate or divinylbenzene), polymers and copolymers of substituted and unsubstituted acrylamides, polymers and copolymers of N-vinylpyrrolidinone, and polyelectrolyte complexes. Hydrogels are described in greater detail in Hydrogels, Kirk-Othmer Encyclopedia of Chemical Technology, 4th Edition, vol. 7, pp. 783-807, John Wiley and Sons, New York, the contents of which are incorporated herein by reference.

The term "hydrogel" is used herein regardless of the state of hydration.

The hydrogel used in connection with the present invention will suitably comprise a substantially water-insoluble, crosslinked, partially neutralized, gel-forming polymer material. Such hydrogel materials can be prepared from polymerisable, unsaturated, acid- and ester-containing monomers. Examples of such monomers are described in more detail below.

The hydrogel used in the present invention preferably comprises a plasticised three-dimensional matrix of cross-linked polymer molecules, and has sufficient structural integrity to be self-supporting even at very high levels of internal water content (e.g. a water content of at least 20%, optionally 50%, by weight) with sufficient flexibility to conform to the surface contours of mammalian skin or other surface with which it is in contact.

The hydrogel generally comprises, in addition to the cross-linked polymeric network, an aqueous or non-aqueous plasticising medium including an organic plasticiser. This plasticising medium is preferably present in the same precursor solution as the monomer(s).

The precursor liquid can comprise a solution of the gel-forming polymer in a relatively volatile solvent, whereby the hydrogel is deposited as a residue on evaporation of the solvent, or—more preferably—the precursor liquid will comprise a solution of the monomer(s), cross-linking agent, plasticiser, and optionally water and other ingredients as desired, whereby the hydrogel is formed by a curing reaction performed on the precursor liquid after application to the substrate to which the hydrogel is to be applied.

In the following discussion, the second form of precursor solution and application protocol (in situ polymerisation of the hydrogel) will be discussed. The solvent deposition method carried out on a pre-formed gel-forming polymer is well known and the details of that procedure do not need to be reproduced here.

The polymerisation reaction is preferably a free-radical polymerisation with cross-linking, which may for example be induced by light, heat, radiation (e.g. ionising radiation), or redox catalysts, as is well known.

For example, the free radical polymerisation may be initiated in known manner by light (photoinitiation), particularly ultraviolet light (UV photoinitiation); heat (thermal initiation); electron beam (e-beam initiation); ionising radiation, particularly gamma radiation (gamma initiation); non-ionising radiation, particularly microwave radiation (microwave initiation); or any combination thereof. The precursor solution may include appropriate substances (initiators), at appropriate levels, e.g. up to about 5% by weight, more particularly between about 0.002% and about 2% by weight, which serve to assist the polymerisation and its initiation, in generally known manner.

Preferred photoinitiators include any of the following either alone or in combination: Type I-hydroxy-ketones and benzilidimethyl-ketals e.g. Irgacure 651. These are believed on irradiation to form benzoyl radicals that initiate polymerisation. Photoinitiators of this type that are preferred are those that do not carry substituents in the para position of the aromatic ring. A particularly preferred photoinitiator is 1-hydroxycyclohexyl phenyl ketone; for example, as marketed under the trade name Irgacure 184 by Ciba Speciality Chemicals. Also preferred are Daracur 1173 (2-hydroxy-2-propyl phenyl ketone) and mixtures of Irgacure 184 and Daracur 1173. Photo-polymerisation is particularly suitable, and may be achieved using light, optionally together with other initiators, such as heat and/or ionizing radiation. Photoinitiation will usually be applied by subjecting the pre-gel reaction mixture containing an appropriate photoinitiation agent to ultraviolet (UV) light. The incident UV intensity, at a wavelength in the range from 240 to 420 nm, is typically greater than about 10 mW/cm$^2$. The processing will generally be carried out in a controlled manner involving a precise predetermined sequence of mixing and thermal treatment or history. The UV irradiation time scale should ideally be less than 60 seconds, and preferably less than 10 seconds to form a gel with better than 95% conversion of the monomers. Those skilled in the art will appreciate that the extent of irradiation will be dependent on a number of factors, including the UV intensity, the type of UV source used, the photoinitiator quantum yield, the amount of monomer(s) present, the nature of the monomer(s) present and the presence of polymerisation inhibitor. In one preferred embodiment, (on the one hand) the precursor solution in contact with the substrate to which it is to be applied and (on the other hand) the source of the polymerisation initiator (e.g. the radiation source) may move relative to one another for the polymerisation step. In this way, a relatively large amount of polymerisable material can be polymerised in one procedure, more than could be handled in a static system. This moving, or continuous, production system is preferred. After completion of the polymerisation, the product is preferably sterilised in conventional manner. The sterile composite may be used immediately, e.g. to provide a skin-adhesive layer in an article, or a top release layer may be applied to the composite for storage and transportation of the composite. If desired, certain ingredients of the hydrogel may be added after the polymerisation and optional cross-linking reaction. However, it is generally preferred that substantially all of the final ingredients of the hydrogel are present in the precursor solution, and that—apart from minor conventional conditioning or, in some cases, subsequent modifications caused by the sterilisation procedure—substantially no chemical modification of the hydrogel takes place after completion of the polymerisation reaction.

Monomers

The gel preferably comprises a polymer having pendant sulphonyl groups, and optionally pendant carboxylic acid groups in acid or salt form. The hydrogel used in the present invention suitably may comprise a substantially water-insoluble, crosslinked, at least partially neutralized, gel-forming polymer material having the pendant sulphonyl groups, and optionally pendant carboxylic groups, in acid or salt form at least at its wound-contacting surface. The hydrogel polymer materials can be prepared from polymerizable, unsaturated, acid- and ester-containing monomers. The hydrogel polymer may be present at the wound-contacting surface of the composition and contain pendant sulphonyl groups, in acid or salt form, and optionally carboxylic groups in acid or salt form. Thus, such monomers include the olefinically unsaturated acids, esters and anhydrides which contain at least one carbon to carbon olefinic double bond. More specifically, these monomers can be selected from olefinically unsaturated carboxylic acids, carboxylic esters, carboxylic acid anhydrides; olefinically unsaturated sulphonic acids; and mixtures thereof.

Olefinically unsaturated carboxylic acid, carboxylic acid ester and carboxylic acid anhydride monomers include the acrylic acids typified by acrylic acid itself, methacrylic acid, ethacrylic acid, α-chloroacrylic acid, α-cyano-acrylic acid, β-methyl-acrylic acid (crotonic acid), α-phenyl acrylic acid, β-acryloxy-propionic acid, sorbic acid, α-chloro-sorbic acid, angelic acid, cinnamic acid, 7-chloro-cinnamic acid, β-styryl-acrylic acid (I-carboxy-4-phenyl-1,3-butadiene), itaconic acid, citraconic acid, mesaconic acid, glutaconic acid, aconitic acid, maleic acid, fumaric acid, tricarboxyethylene and maleic acid anhydride and salts (e.g. alkali metal salts such as sodium, potassium and lithium salts) thereof. For forming any polymer to be present at the lesion-contacting surface of the composition, the monomer or monomer mixture will include a monomer containing pendant sulphonyl groups, e.g. —SO3" in acid or salt form.

Olefinically unsaturated sulphonic acid monomers include aliphatic or aromatic vinyl sulphonic acids such as vinylsulphonic acid, allylsulphonic acid, vinyltoluenesulphonic acid and styrene sulphonic acid; vinyl sulphobetaines such as SPDA (1-propanaminium N,N-dimethyl-N-[2-[(1-oxo-2-propenyl)oxy]-3-sulfo hydroxide, inner salt (available from Raschig); acrylic and methacrylic sulphonic acid such as sulphoethyl acrylate, sulphoethyl methacrylate, sulphopropyl acrylate, sulphopropyl methacrylate, 2-hydroxy-3-acryloxy propyl sulphonic acid, 2-hydroxy-3-methacryloxy propyl sulphonic acid and 2-acrylamido-2-methyl-propanesulphonic acid and salts (e.g. ammonium or alkali metal salts, such as sodium, potassium and lithium salts, or alkaline earth metal salts, such as calcium or magnesium) thereof.

The monomers may suitably be used in admixture with each other or with other monomers. In one particularly useful embodiment of the invention, a monomer which has a first counter-cation associated with it may be used in admixture with one or more monomer which has/have one or more second/further counter-cation(s) associated with it/them. The first counter-cation and the second/further counter cation may be the same or different. The monomers in their anionic form (i.e. disregarding the counter-cation) may be the same or different. In this way, the proportions of different cations (e.g. alkali metal ions such as sodium or potassium, or ammonium ions) can be finely controlled in the resultant polymer (homopolymer or copolymer). The particular weight ratios of one monomer to the or each other monomer can be selected within wide limits by those skilled in the art, depending on the desired properties of the resultant hydrogel polymer.

Further examples of suitable monomers for use in the present invention include: a polyalkylene glycol acrylate or a substituted derivative thereof; a polyalkylene glycol methacrylate or a substituted derivative thereof; acrylic acid and salts thereof (e.g. alkali metal salts such as sodium, potassium and lithium salts); 2-acrylamido-2-methyl-propanesulphonic acid and salts thereof (e.g. ammonium or alkali metal salts, such as sodium, potassium and lithium salts, or alkaline earth metal salts, such as calcium or magnesium); acrylic acid (3-sulphopropyl) ester or a substituted derivative thereof or a salt thereof (e.g. an alkali metal salt such as sodium, potassium or lithium salt); diacetone acrylamide (N-1,1-dimethyl-3-oxobutyl-acrylamide); a vinyl lactam (e.g. N-vinyl pyrrolidone or a substituted derivative thereof); an optionally substituted N-alkylated acrylamide such as hydroxyethyl acrylamide; and an optionally substituted N,N-dialkylated acrylamide; and/or N-acryloyl morpholine or a substituted derivative thereof. For forming any polymer of the hydrogel, which may in use contact the wound, the monomer or monomer mixture may include a monomer containing pendant sulphonyl groups, e.g. —$SO_3^-$ in acid or salt form, and optionally carboxylic groups in acid or salt form.

Particularly preferred monomers include: the sodium salt of 2-acrylamido-2-methylpropane sulphonic acid, commonly known as NaAMPS, which is available commercially at present from Lubrizol as either a 50% aqueous solution (reference code LZ2405) or a 58% aqueous solution (reference code LZ2405A); acrylic acid (3-sulphopropyl) ester potassium salt, commonly known as SPA or SPAK (SPA or SPAK is available commercially in the form of a pure solid from Raschig); acrylic acid (3-sulphopropyl) ester sodium salt, commonly known as SPANa (SPANa is available in the form of a pure solid from Raschig); N-acryloyl morpholine; and hydroxyethyl acrylamide.

The above monomers and monomer types may optionally include substituent groups. Optional substituents of the monomers used to prepare the hydrogels used in the present invention may preferably be selected from substituents which are known in the art or are reasonably expected to provide polymerisable monomers which form hydrogel polymers having the properties necessary for the present invention. Suitable substituents include, for example, lower alkyl (e.g. $C_1$ to $C_{10}$, optionally $C_1$ to $C_5$), hydroxy, halo and amino groups.

Cross-Linking Agents

Conventional cross-linking agents are suitably used to provide the necessary mechanical stability and to control the adhesive properties of the hydrogel. The amount of cross-linking agent required will be readily apparent to those skilled in the art such as from about 0.01% to about 0.5%, particularly from about 0.05% to about 0.4%, most particularly from about 0.08% to about 0.3%, by weight of the total polymerisation reaction mixture. Typical cross-linkers include tripropylene glycol diacrylate, ethylene glycol dimethacrylate, triacrylate, polyethylene glycol diacrylate (polyethylene glycol (PEG) molecular weight between about 100 and about 4000, for example PEG400 or PEG600), and methylene bis acrylamide.

Organic Plasticisers

The hydrogel and/or its pre-gel may comprise one or more organic plasticisers. The one or more organic plasticisers may suitably comprise any of the following either alone or in combination: at least one polyhydric alcohol (such as glycerol, polyethylene glycol, or sorbitol), at least one ester derived therefrom, at least one polymeric alcohol (such as polyethylene oxide) and/or at least one mono- or poly-alkylated derivative of a polyhydric or polymeric alcohol (such as alkylated polyethylene glycol). Glycerol is the preferred plasticiser. An alternative preferred plasticiser is the ester derived from boric acid and glycerol. When present, the organic plasticiser may comprise up to about 45% by weight of the hydrogel composition.

Surfactants

Any compatible surfactant may optionally be used as an additional ingredient of the hydrogel composition. Surfactants can lower the surface tension of the mixture before polymerisation and thus aid processing. The surfactant or surfactants may be non-ionic, anionic, zwitterionic or cationic, alone or in any mixture or combination. The surfactant may itself be reactive, i.e. capable of participating in the hydrogel-forming reaction. The total amount of surfactant, if present, is suitably up to about 10% by weight of the hydrogel composition, preferably from about 0.05% to about 4% by weight.

In a preferred embodiment of the invention the surfactant comprises at least one propylene oxide/ethylene oxide block copolymer, for example such as that supplied by BASF Plc under the trade name Pluronic P65 or L64.

Other Additives

The hydrogel in the composite of the present invention may include one or more additional ingredients, which may be added to the pre-polymerisation mixture or the polymerised product, at the choice of the skilled worker. Such additional ingredients are selected from additives known in the art, including, for example, water, organic plasticisers, surfactants, polymeric material (hydrophobic or hydrophilic in nature, including proteins, enzymes, naturally occurring polymers and gums), synthetic polymers with and without-pendant carboxylic acids, electrolytes, pH regulators, colourants, chloride sources, bioactive compounds and mixtures thereof. The polymers can be natural polymers (e.g. xanthan gum), synthetic polymers (e.g. polyoxypropylene-polyoxyethylene block copolymer or poly-(methyl vinyl ether alt maleic anhydride)), or any combination thereof. By "bioactive compounds" we mean any compound or mixture included within the hydrogel for some effect it has on living systems, whether the living system be bacteria or other microorganisms or higher animals such as the patient. Bioactive compounds that may be mentioned include, for example, pharmaceutically active compounds, antimicrobial agents, antiseptic agents, antibiotics and any combination thereof. Antimicrobial agents may, for example, include: sources of oxygen and/or iodine (e.g. hydrogen peroxide or a source thereof and/or an iodide salt such as potassium iodide) (see, for example Bioxzyme technology, for example in The Sunday Telegraph (UK) 26 Jan. 2003 or the discussion of the Oxyzyme system at www.wounds-uk.com/posterabstracts2003.pdf); honey (e.g. active Manuka honey); antimicrobial metals, metal ions and salts, such as, for example, silver-containing antimicrobial agents (e.g. colloidal silver, silver oxide, silver nitrate, silver thiosulphate, silver sulphadiazine, or any combination thereof); or any combination thereof.

In the Bioxzyme system, a dressing comprises two hydrogels. One contains glucose based antibacterial compounds and the other contains enzymes that convert the glucose into hydrogen peroxide. When these are exposed to air and contacted together at a wound site, the enzyme-containing gel being adjacent the skin and the glucose-containing gel overlying the enzyme-containing gel, a low level steady flow of hydrogen peroxide is produced, which inhibits anaerobic bacteria. This antibacterial effect can be enhanced by the inclusion of a very low level of iodide (less than about 0.04%) in the hydrogel. The hydrogen peroxide and the iodide react to produce iodine, a potent antimicrobial agent.

Hydrogels incorporating antimicrobial agents may, for example, be active against such organisms as Staphylococcus aureus and Pseudomonas aeruginosa.

Agents for stimulating the healing of wounds and/or for restricting or preventing scarring may be incorporated into the hydrogel. Examples of such agents include growth factors e.g. from GroPep Ltd, Australia or Procyte, USA (see, e.g. WO-A-96/02270, the contents of which are incorporated herein by reference); cell nutrients (see, e.g., WO-A-93/04691, the contents of which are incorporated herein by reference); glucose (see, e.g., WO-A-93/10795, the contents of which are incorporated herein by reference); an anabolic hormone or hormone mixture such as insulin, triiodothyronine, thyroxine or any combination thereof (see, e.g., WO-A-93/04691, the contents of which are incorporated herein by reference); or any combination thereof.

Additional polymer(s), typically rheology modifying polymer(s), may be incorporated into the polymerisation reaction mixture at levels typically up to about 10% by weight of total polymerisation reaction mixture, e.g. from about 0.2% to about 10% by weight. Such polymer(s) may include polyacrylamide, poly-NaAMPS, polyethylene glycol (PEG), polyvinylpyrrolidone (PVP) or carboxymethyl cellulose.

The hydrogel used in the present invention may consists essentially of a cross-linked hydrophilic polymer of a hydrophilic monomer and optionally one or more comonomer, together with water and/or one or more organic plasticiser, and optionally together with one or more additives selected from surfactants, polymers, pH regulators, electrolytes, chloride sources, bioactive compounds and mixtures thereof, with less than about 30%, optionally less than about 20%, optionally less than 10% by weight of other additives.

The water activity, which is related to the osmolarity and the ionic strength of the precursor solution (as measured, for example, by a chilled mirror dewpoint meter, Aqualab T3) is preferably between 0.05 and 0.99, more preferably between 0.2 and 0.99, and even more preferably between 0.3 and 0.98. The higher the ionic strength, reflected in a lower water activity, the lesser the swelling of the fibre structure. The ionic strength of the precursor solution can therefore be used to optimise the hydrogel composite properties.

For further details of the hydrogel material for use in the present invention, and its preparation, please refer to the following publications: PCT Patent Applications Nos. WO-97/24149, WO-97/34947, WO-00/06214, WO-00/06215, WO-00/07638, WO-00/46319, WO-00/65143, WO-01/96422 and WO 2007/007155, the disclosures of which are incorporated herein by reference.

One or more porous sheets, for example a scrim, may be disposed within or on a surface of one or more of the layers, preferably the first layer, and preferably within or on a surface of the gel material, preferably a hydrogel material. A scrim includes, but is not limited to, porous sheets comprising materials selected from woven, non-woven and net materials. Such a scrim material may be formed of a material that is natural in origin, synthetic in origin, or partly natural and partly synthetic. The scrim may suitably be in the form of a net or a woven or non-woven fabric. Preferred scrims include those formed from polyolefins, polyamides, polyacrylates, or polyesters, for example non-wovens, foams or nets. Suitable non-woven scrims are available from HDK Industries Inc. (USA). The scrim material may, for example, comprise sodium polyacrylate fibres, such as those commercially available under the tradename Oasis™ from Acordis Technical Absorbents Limited. The scrim is preferably provided by introducing it into a laid down (e.g. cast) layer of a pre-gel liquid precursor for the hydrogel material, before curing, so that the liquid pre-gel covers and surrounds the scrim. On curing of the liquid pre-gel, the hydrogel is thereby formed encapsulating the scrim material. Use of a scrim material in this way is found to be potentially helpful in enhancing the strength and ease of handling of the hydrogel component and/or the finished dressing.

A scrim may also be preferably present on the surface of the first layer that, in use, faces away from the wound and toward the second layer. The presence of this scrim has been found to enhance the adhesion of the first layer to any other layers and materials with which it may be in contact, e.g. the second layer or a pressure sensitive adhesive disposed between the scrim and the second layer.

The second layer and/or second material preferably comprises a film of material of Shore Hardness on the A scale greater than 40, preferably greater than 50 even more preferably greater than 60, as measured using ASTM method D2240. Suitable materials for use in the second layer include, but are not limited to, polyester, polyurethane, polystyrene, polycarbonate and the like. The second layer may optionally be coated with a pressure sensitive adhesive for example acrylic or rubber based adhesive, for adhesion to one or more other layers in the layered composition. Examples of suitable adhesive coated materials for the second layer include PPI-10260 Polyester Self Adhesive tape and PPI 10426 Polyester Self Adhesive Tape from PPI Adhesive Products Ltd (Ireland).

The first material may be in the form of a sheet, which may be continuous or discontinuous, and disposed over part or all of the second layer.

The second material may be in the form of a sheet, which may be continuous or discontinuous, and disposed over part or all of the second layer and/or part or all of the third layer.

The third material may be in the form of a sheet, which may be continuous or discontinuous, and disposed over part or all of the second layer.

The third layer and/or third material preferably comprises a film material. Suitable film materials include polyurethanes. The third layer may have a lower tensile modulus than the second layer. The third material may have a lower tensile modulus than the second material. The tensile modulus of a material is the Young's modulus of the material when under tensile force. Measurement of the tensile modulus of a material is known to those skilled in the art. The measurement may be carried out using standard equipment, and may be carried out at standard temperature and pressure, for example 20° C. and 101.325 kPa. The tensile modulus may be measured in accordance with ASTM D 882. The third material may elongate in a lateral direction more readily than the second material under the same conditions. The third layer may elongate in a lateral direction more readily than the second layer under the same conditions. Under the same conditions, the force required to elongate the third layer in a lateral direction by 20% is preferably about 80% or less, more preferably about 70% or less and even more preferably about 50% or less, than that required to elongate the second layer by 20%. Under the same conditions, the force required to elongate the third layer in a lateral direction by 50% is preferably about 80% or less, more preferably about 70% or less and even more preferably about 50% or less, than that required to elongate the second layer by 50%. Under the same conditions, the force required to elongate the third layer in a lateral direction by 100% is preferably about 80% or less, more preferably about 70% or less and even more preferably about 50% or less, than that required to elongate the second layer by 100%.

Under the same conditions, the force required to elongate the third material in a lateral direction by 20% is preferably about 80% or less, more preferably about 70% or less and even more preferably about 50% or less, than that required to elongate the second material by 20%. Under the same conditions, the force required to elongate the third material in a lateral direction by 50% is preferably about 80% or less, more preferably about 70% or less and even more preferably about 50% or less, than that required to elongate the second material by 50%. Under the same conditions, the force required to elongate the third material in a lateral direction by 100% is preferably about 80% or less, more preferably about 70% or less and even more preferably about 50% or less, than that required to elongate the second material by 100%.

The third material may be a low friction material, preferably in the form of a sheet. The low friction material is preferably such that clothing materials, such as cotton and/or polyester can pass easily over the surface of the material. A low friction material includes, but is not limited to, a material having a low coefficient of friction, which may be a static or dynamic coefficient of friction, for example against a cotton or Teflon material. Measurement of static and dynamic coefficients of friction are known to those skilled in the art. The static and dynamic coefficients of friction may be measured using standard equipment, and may be carried out at standard temperature and pressure, for example 20° C. and 101.325 kPa. The static and dynamic coefficients of friction may be measured in accordance with ASTM D1894-08. Against a cotton material, the dynamic coefficient of friction of the third material may be about 1.5 or less, optionally about 1 or less, optionally about 0.9 or less. Against a Teflon material, the dynamic coefficient of friction of the third material may be about 1 or less, optionally about 0.7 or less, optionally about 0.5 or less, optionally about 0.4 or less.

The third material may have a low friction value as measured in accordance with ISO 8295, 1986, in the test described in U.S. Pat. No. 5,643,187 in column 11, lines 18 to 21. The friction may be measured as the dynamic friction according to ISO 8295, 1986, the base used being a teflon coated glass tissue of the type: Acoflon G 13 A from Aco-plast A/S, Helsingor, DK, the weight of the carriage being 500 g. This test may be carried out at standard temperature and pressure, for example 20° C. and 101.325 kPa. The frictional value of the third material, for example when in the form of a sheet, in N, when measured in accordance with this test may be about 5 or less, preferably about 3 or less, more preferably about 2 or less.

The surface of the third layer which, in use, faces the wound is preferably coated with a pressure sensitive adhesive, for adhesion to one or more other layers with which it may be in contact and/or for adhesion to the skin. Suitable third layer materials coated with pressure sensitive adhesives include for example Inspire 2317 from Exopack.

The layered composition may also be termed a layered composite.

The present invention will now be illustrated with reference to the following non-limiting Example.

EXAMPLE

A viscolelastic gel was made by curing the following pre-gel formulation.

Pre-gel: 67 parts by weight of 58% aqueous solution of the sodium salt of acrylamidomethyl-propanesulphonic acid (NaAMPS, LZ2405 Lubrizol), 0.5 parts acrylic acid (3-sulphopropyl) ester potassium salt, commonly known as SPA or SPAK (SPA or SPAK is available commercially in the form of a pure solid from Raschig), 30 parts glycerol, these ingredients are mix A. Into 100 g of mix A 0.11 g of a 2 to 10 (by weight) mixture of Daracure 1173 photoinitiator (Ciba Speciality Chemicals) and IRR280 cross-linker (PEG400 diacrylate, UCB Chemicals) is added and stirred for one hour.

The hydrogel viscoelastic gel layer was then assembled in the following manner.

A glass petri dish was (circa 9 cm diameter) lined with a siliconised polyester film. Circa 1.5 to 2 g of the following pre-gel formulation was evenly spread across the petri dish. A polyester scrim (HDK D1451, circa 9 cm diameter) was placed on top of the pre-gel coated polyurethane (scrim high). About 4 to 5 g of the following pre-gel formulation were evenly spread into the lined petri dish on top of the polyester scrim. The hydrogel was then cured with a medium pressure mercury arc lamp located within a bench top UV curing machine (NUVA-Solo-30) GEW, UK) at a conveyer speed of 7 m/minute.

A 40 mm by 30 mm rectangle of the above viscoelastic gel layer was overlaid with a 40 mm by 30 mm rectangle of PPI 10426 polyester such that the adhesive side was in contact with the scrim high surface of the viscoelastic gel. Overlaid onto the PPI polyester surface was a 70 mm by 40 mm rectangle of Inspire 2317 and the paper backing of the latter removed.

The dressing had a low friction surface as assessed by running a fingernail over the outer layer and excellent penetration resistance as a assessed by the lack of penetration of a HB pencil.

The dressing was then applied to the blistered heel of a male patient. The patient reported significant relief from discomfort when wearing footware. After 24 hours the blister had improved significantly with respect to healing. The viscoelastic gel was found to be intact.

In contrast covering the blister with a dressing constructed without the PPI Polyester adhesive intermediate layer was found to be uncomfortable and after 24 hours wear the viscoelastic gel was found to have undergone some break up.

The foregoing broadly describes the invention without limitation. Variations and modifications as will be readily apparent to those skilled in this art are intended to be covered by the scope of the present invention as defined in and by the following claims.

The invention claimed is:

1. A layered composition comprising:
   a first layer comprising a first material, wherein the first material comprises a gel material;
   a second layer comprising a sheet of a polymeric second material; and
   a third layer comprising a third material, which is a low friction material,
   wherein the second layer is disposed between the first and third layers;
   and wherein the layered composition has a microhardness between about 30 International Rubber Hardness Degrees (IRHD) and about 90 IRHD.

2. A layered composition according to claim 1, wherein the second material is a polyester.

3. A layered composition according to claim 1, wherein the layered composition has a microhardness between about 50 IRHD and about 90 IRHD.

4. A layered composition according to claim 1, wherein the gel material comprises a hydrogel or hydrocolloid.

5. A layered composition according to claim 1, wherein the gel material consists of a hydrogel or hydrocolloid.

6. A layered composition according to claim 1, wherein the third material has a lower tensile modulus than the second material.

7. A layered composition according to claim 1, wherein the third material is a low friction material.

8. A method for the prevention, dressing or treatment of a wound comprising administering to the surface of the wound the layered composition of claim 1.

9. The method according to claim 8, wherein the wound is selected from the group consisting of skin cuts, grazes, abrasions, tears, burns, scalds, ulcers, spots, blisters and chafes, whether the wound is dermal, epidermal, or a combination of both, and whether the wound is acute or chronic.

10. The method according to claim 8 or 9, wherein the layered composition is adapted so that the first layer is in fluid flow communication with the wound or skin of a wearer in use.

11. A wound dressing comprising the layered composition according to claim 1.

12. The layered composition of claim 1, or a wound dressing according to claim 11, wherein the second layer comprises at least one of the properties: (a) promotes wound healing, (b) avoids or mitigates break-up of the gel material of the first layer, (c) enhances penetration resistance of the composition or dressing, (d) facilitates improved dispersion of external forces applied to the composition or dressing, (e) provides a base for mounting the third layer thereto to provide acceptable slip properties of the layered composition dressing against clothing when worn by a user on the skin, or (f) imparts mechanical stability to the gel material of the first layer.

13. A method of manufacturing a layered composition of claim 1, comprising assembling the first, second and third layers to form the layered composition, optionally with adhering the first, second and third layers together, optionally with one or more further layers and/or materials or adhesive materials, disposed between the first and second layer and/or the second and third layer.

14. A method of preventing, dressing or treating a wound comprising applying a composition according to claim 1 or a wound dressing according to claim 11 to a wound and/or skin of a wearer, wherein the first layer is disposed closer to the wound and/or skin than the third layer and the first layer is preferably in fluid flow communication with the wound and/or skin.

* * * * *